＝

US008202534B2

(12) United States Patent
Chowdhury et al.

(10) Patent No.: US 8,202,534 B2
(45) Date of Patent: *Jun. 19, 2012

(54) ATTACHMENT OF A HANDLE TO A SOLID ORAL DOSAGE FORM

(75) Inventors: Tahseen A. Chowdhury, Washington Township, NJ (US); Edward J. Gabrielski, Bound Brook, NJ (US); Christopher H. Baker, Forest, VA (US)

(73) Assignee: Teva Women's Health, Inc., Woodcliff Lake, NJ (US)

( * ) Notice: Subject to any disclaimer, the term of this patent is extended or adjusted under 35 U.S.C. 154(b) by 1780 days.

This patent is subject to a terminal disclaimer.

(21) Appl. No.: 11/446,510

(22) Filed: Jun. 5, 2006

(65) Prior Publication Data

US 2006/0280792 A1 Dec. 14, 2006

Related U.S. Application Data

(60) Provisional application No. 60/686,976, filed on Jun. 3, 2005.

(51) Int. Cl.
*A61K 9/00* (2006.01)
(52) U.S. Cl. ......... 424/464; 426/104; 426/134; 426/421
(58) Field of Classification Search .................. 424/464; 514/948
See application file for complete search history.

(56) References Cited

U.S. PATENT DOCUMENTS

| | | | |
|---|---|---|---|
| 2,637,281 A | | 5/1953 | Leo Latini et al. |
| 3,557,267 A | | 1/1971 | Angelotti et al. |
| 3,972,758 A | | 8/1976 | Bieber |
| 4,478,822 A | | 10/1984 | Haslam et al. |
| 4,548,771 A | | 10/1985 | Senapati et al. |
| 4,671,953 A | | 6/1987 | Stanley et al. |
| 4,885,173 A | | 12/1989 | Stanley et al. |
| 5,132,114 A | | 7/1992 | Stanley et al. |
| 5,211,892 A | * | 5/1993 | Gueret .......................... 264/443 |
| 5,298,256 A | | 3/1994 | Flockhart et al. |
| 5,711,961 A | | 1/1998 | Reiner et al. |
| 6,019,154 A | | 2/2000 | Ma et al. |
| 6,077,144 A | | 6/2000 | Fishman |
| 6,156,359 A | | 12/2000 | Segal |
| 6,802,920 B2 | | 10/2004 | Shinohara et al. |
| 2004/0213828 A1 | | 10/2004 | Smith |
| 2008/0213358 A1 | | 9/2008 | Arkenau-Maric et al. |

FOREIGN PATENT DOCUMENTS

| | | |
|---|---|---|
| GB | 636 219 A | 4/1950 |
| JP | 2003-320496 A | 11/2003 |
| WO | WO 2006/100274 A1 | 9/2006 |

OTHER PUBLICATIONS

"Application Technology," webpage available at http://www.staplaultrasonics.com/c6-app/app.htm, STAPLA Ultrasonics Corporation, STAPLA Ultrasonics Corporation, 3 pages (accessed Aug. 2004).
"Introduction: A broad field of applications," webpage available at http://www.staplaultrasonics.com/intro/intro.htm, STAPLA Ultrasonics Corporation, STAPLA Ultrasonics Corporation, 2 pages (accessed Aug. 2004).
"Ultrasonic Systems," http://www.branson-plasticsjoin.com/ultrasonic.html, Branson Ultrasonics Corporation, Branson Ultrasonics Corporation, 6 pages (accessed Aug. 2004).
Co-pending U.S. Appl. No. 11/556,378, filed Nov. 3, 2006.
International Search Report for International Application No. PCT/US2007/022428, mailed Jun. 2, 2008, 4 pgs.
Written Opinion of the International Searching Authority for International Application No. PCT/US2007/022428, mailed Jun. 2, 2008, 7 pgs.
International Search Report for International Application No. PCT/US2006/021658, mailed Oct. 12, 2006, 2 pgs.
Written Opinion of the International Searching Authority for International Application No. PCT/US2006/021658, mailed Oct. 12, 2006, 6 pgs.
Office Action dated Aug. 9, 2010, issued in U.S. Pat. Appl. No. 11/556,378, to Chowdhury et al., filed Nov. 3, 2006.
English language Abstract for Japanese Patent Publication No. JP 2003-320496 A, Japanese Patent Office, Patent & Utility Model Gazette, Patent Abstracts of Japan, (2003).

* cited by examiner

*Primary Examiner* — James Rogers
(74) *Attorney, Agent, or Firm* — Sterne, Kessler, Goldstein & Fox P.L.L.C.

(57) ABSTRACT

The present invention relates to a method of attaching a handle to a solid oral dosage form by use of high frequency mechanical vibrations. The present invention also relates to a method of attaching a handle to a solid oral dosage form, the method comprising: (a) placing a handle in contact with a solid oral dosage form, wherein an area of contact between the handle and the solid oral dosage form forms a joint interface; (b) applying high frequency mechanical vibrations to the joint interface until the solid oral dosage form at the joint interface reaches a molten state; and (c) cooling the joint interface in a molten state to allow solidification, thereby attaching the handle to the solid oral dosage form.

22 Claims, No Drawings

ATTACHMENT OF A HANDLE TO A SOLID ORAL DOSAGE FORM

This application claims the benefit of the filing date of U.S. Appl. No. 60/686,976, filed Jun. 3, 2005, which is incorporated by reference herein in its entirety.

BACKGROUND OF THE INVENTION

1. Field of the Invention

The present invention relates to a method of making a solid oral dosage form attached to a handle by use of high frequency mechanical vibrations. The present invention also relates to a method of attaching a handle to a solid oral dosage form, the method comprising: (a) placing the handle in contact with the solid oral dosage form, wherein an area of contact between the handle and the solid oral dosage form forms a joint interface; (b) applying high frequency mechanical vibrations to the joint interface until the solid oral dosage form at the joint interface reaches a molten state; and (c) cooling the joint interface in a molten state to allow solidification, thereby attaching the handle to the solid oral dosage form.

2. Background Art

Numerous active agent delivery forms exist for administration of active agents to a subject. The majority of active agents are administered either via (1) oral administration to the gastrointestinal (GI) tract by ingestible tablets or capsules or (2) by injection. Neither of these administration routes are effective in all cases, and both administration routes suffer from several disadvantages.

For oral administration to the GI tract, one disadvantage is that there is normally a substantial delay between the time of oral administration and the time that the therapeutic effect of the active agent begins. Another difficulty encountered in administering active agents orally to the GI tract is that dosages are prepared or determined for use with an "average" patient. Most active agents have widely varying effects on different patients. The result can be underdosing or overdosing a particular patient.

Additionally, there are disadvantages associated with injections. Many patients, particularly children and geriatric adults, have an aversion to injections. In some patients, this aversion can be so pronounced as to make the use of injections a serious concern. Since intense psychological stress can exacerbate a patient's debilitated condition, it sometimes becomes undesirable to use injections where the patient is seriously ill or suffers from a debilitating condition or injury.

As an alternative to administration to the GI tract and injections, administration to the mucosa of the oral cavity has been used. One advantage of oral mucosa delivery is that it is a non-invasive active agent delivery method that can be administered by the caregiver or the patient with minimal discomfort. Furthermore, oral mucosa delivery has better patient compliance, less risk of infection and lower cost than invasive procedures such as injection and implantation. It also has a much shorter onset time, i.e., the time from administration to therapeutic effect, than does oral delivery to the GI tract. An active agent absorbed via the oral mucosa will also avoid first pass metabolism, in which the active agent is metabolized in the GI tract and liver.

Administration of active agents via the oral mucosa does not expose the active agent to the gastric and intestinal digestive juices. Commercial examples of active agent formulations delivered via the oral mucosa include Oralet® (Abbott Laboratories, Abbott Park, Ill.) and Actiq® (Cephalon Inc., Salt Lake City, Utah).

Oral transmucosal delivery forms, such as sublingual tablets, troches, lozenges, lozenges-on-a-stick, chewing gums, and buccal patches, have been described previously. U.S. Pat. No. 5,711,961 to Reiner, et al. discloses a chewing gum for delivery of active agents. Oral transmucosal delivery using a buccal patch is disclosed in U.S. Pat. No. 5,298,256 to Flockhart, et al. Lozenges and tablets are commonly used for oral transmucosal delivery of active agents. For example, nitroglycerin sublingual tablets have been on the market for many years.

A solid oral dosage form attached to a handle, a.k.a., a lollipop or lozenge-on-a-stick, for transmucosal active agent delivery is disclosed in U.S. Pat. No. 4,671,953. In addition to being non-invasive and providing a particularly easy method of delivery, the solid oral dosage form attached to a handle allows a patient or caregiver to move the dose in and out of the mouth to titrate the dose. This practice is called dose-to-effect, in which a patient or caregiver controls the administration of the dose until the expected therapeutic effect is achieved. The practice of dose-to-effect is particularly important for certain symptoms, such as pain, nausea, motion sickness, and premedication prior to anesthesia because each patient needs a different amount of medication to treat these symptoms. Once the appropriate amount of active agent is delivered, the patient or caregiver can remove the solid oral dosage form, thus stopping the active agent delivery to prevent overdose.

A common concern with medicated solid oral dosage forms attached to a handle is the possibility that the solid oral dosage form part of the device will become detached from the handle. If the solid oral dosage form becomes detached from the handle, then it can be more difficult to remove and/or administer the active agent as desired. Also of concern is the possibility that the solid oral dosage form which is detached from its handle could be swallowed in its entirety, possibly resulting in an overdosing of the active agent. Similarly, a detached solid oral dosage form could also become a choking hazard.

BRIEF SUMMARY OF THE INVENTION

The present invention is directed to a method of attaching a handle to a solid oral dosage form by applying high frequency mechanical vibrations. The invention is also directed to a method of attaching a handle to a solid oral dosage form, the method comprising: (a) placing the handle in contact with the solid oral dosage form, wherein an area of contact between the handle and the solid oral dosage form forms a joint interface; (b) applying high frequency mechanical vibrations to the joint interface until the solid oral dosage form at the joint interface reaches a molten state; and (c) cooling the joint interface in a molten state to allow solidification, thereby attaching the handle to the solid oral dosage form.

DETAILED DESCRIPTION OF THE INVENTION

The present invention is directed to a method for attaching a handle to a solid oral dosage form by use of high frequency mechanical vibrations.

High frequency mechanical vibrations are used to melt materials using friction between the parts in contact, causing a localized melting between at least one of the materials. The parts are then held in contact by pressure until the material cools down and forms a bond. Creation of the bond increases the attachment of the solid oral dosage form to the handle, thus reducing the probability that the solid oral dosage form will become detached from the handle.

The present invention is also directed to a method of attaching a handle to a solid oral dosage form, the method comprising attaching the handle to the solid oral dosage form by applying high frequency mechanical vibrations. In some embodiments, the invention is directed to a method of attaching a handle to a solid oral dosage form, the method comprising: (a) placing the handle in contact with the solid oral dosage form, wherein an area of contact between the handle and the solid oral dosage form forms a joint interface; (b) applying high frequency mechanical vibrations to the joint interface until the solid oral dosage form at the joint interface reaches a molten state; and (c) cooling the joint interface in a molten state to allow solidification, thereby attaching the handle to the solid oral dosage form. The present invention is also directed to a solid oral dosage form attached to a handle made by the method of the present invention.

The term "solid oral dosage form" refers to a solid object of a size capable of being placed in an oral cavity, the solid object comprising a matrix capable of releasing an active agent. In some embodiments, the matrix can be substantially free of allergens and additives such as synthetic flavorings, dyes, preservatives, and alcohols.

The solid oral dosage form can be comprised of various materials, as long as at least one of the materials in the dosage form is meltable. As used herein, "meltable" refers to the physical property of the material such that the material can undergo a physical change, e.g., from a solid state to a liquid state, with a change in temperature. In some embodiments, the meltable material can melt at a temperature of about 25° C. to about 200° C., or about 40° C. to about 180° C. In some embodiments, the meltable material can melt at an elevated temperature of from about 50° C. to about 200° C., or about 75° C. to about 150° C. In some embodiments, the meltable material undergoes a physical changes at a temperature that is at least about 25° C. above room temperature. "Non-meltable" means all pharmaceutically acceptable materials having a melting point above 220° C. and those materials that decompose instead of melting. In some embodiments, the meltable material will resolidify when the compound is returned to a temperature below the temperature at which the melting occurred. As used herein, a solid oral dosage form comprising a meltable material is a solid or semisolid at room temperature (about 25° C.). These meltable materials can be further classified as either hydrophilic or hydrophobic.

Suitable meltable hydrophilic materials for use in the present invention include povidone, polyethylene glycol, and mixtures thereof. Suitable meltable hydrophobic materials for use in the present invention include magnesium stearate, calcium stearate, aluminum stearate, hydrogenated vegetable oil, and mixtures thereof.

In some embodiments, the amount of meltable material, either hydrophilic, hydrophobic, or a mixture thereof, present in the oral dosage form is about 1% to about 95% of the weight of the solid oral dosage form. In some embodiments, the meltable material present in the oral dosage form is about 1% to about 75%, or about 1% to about 55%, or about 1% to about 35%, or about 1% to about 15% of the weight of the solid oral dosage form. In some embodiments, the meltable material is about 15% of the weight of the solid oral dosage form. In some embodiments, the meltable material present in the oral dosage form is about 5% to about 95%, or about 10% to about 80%, or about 15% to about 60%, or about 15% to about 40% of the weight of the solid oral dosage form.

In some embodiments, the solid oral dosage form comprises a carbohydrate-free matrix. In some embodiments, the carbohydrate-free matrix is povidone. In some embodiments, the carbohydrate-free matrix comprises an artificial sweetener. In some embodiments, the solid oral dosage form is a "sugar-free solid oral dosage form" or "carbohydrate-free solid oral dosage form." The terms "sugar-free solid oral dosage form" or "carbohydrate-free solid oral dosage form" refer to dosage forms that are substantially free of carbohydrates. Substantially free of carbohydrates means that the dosage form contains less than about 5.0% by weight of carbohydrate. In some embodiments, substantially free of carbohydrates means the dosage form contains less than about 3% by weight, or less than about 2% by weight, or even less than about 1% by weight of carbohydrate. In some embodiments, the term substantially free of carbohydrates means that the dosage form contains no carbohydrates. In some embodiments, the dosage form contains less than 0.5 g of carbohydrates per dosage form. In some embodiments, the matrix comprises a carbohydrate-containing matrix. As used herein, the term "carbohydrate" refers to compounds that are polyhydroxy aldehydes or ketones, or substances that yield such compounds on hydrolysis. Many, but not all, carbohydrates have the empirical formula $(CH_2O)_n$. Some carbohydrates can also contain nitrogen, phosphorous, or sulfur as described in *Lehninger: Principles of Biochemistry*, W. H. Freeman and Company, 4$^{th}$ ed. (2005), herein incorporated by reference. The major classes of carbohydrates include monosaccharides, disaccharides, oligosaccharides, and polysaccharides. All four classes are considered by the present invention as carbohydrates. For example, in some embodiments the solid oral dosage form comprising a carbohydrate matrix can comprise starch, sucrose, fructose, or combinations thereof.

In some embodiments, the solid oral dosage form can comprise an excipient. In some embodiments, the excipient can be, but is not limited to, an absorbent, buffering agent, colorant, flavorant, solvent, coating agent, direct compression agent, disintegrant, glidant, lubricant, opaquant, suspending agent, sweetening agent, anti-adherent, binder, preservative, or combinations thereof.

The term "attached" refers to the fastening of the handle to the solid oral dosage form. The attachment bond strength can vary. In some embodiments, about 1 pound to about 70 pounds of force is required to detach the handle from the solid oral dosage form. In some embodiments, about 5 pounds to about 70 pounds of force is required to detach the handle from the solid oral dosage form. The attachment bond strength is determined by a "pull force tester, such as a Chatillon TCD 201 MF Series Tester stand and Chatillon DFA-50 digital force gauge (Chatillon Force Measurement Systems, Largo, Fla.).

The term "handle" refers to any feature of the device, distinct in composition from the solid oral dosage form, which protrudes from the solid oral dosage form which allows an individual to insert and remove the solid oral dosage form from an oral cavity. In some embodiments, the term "handle" refers to a means for removing the solid oral dosage form from an oral cavity. In some embodiments, the handle is rigid, e.g., a stick or rod. In some embodiments, the handle is flaccid, e.g., a string or cord. The handle can vary in shape. In some embodiments, the handle is relatively straight. In some embodiments, the handle is ring-shaped. In some embodiments, the handle is malleable, and can be bent or altered to achieve a desired shape. The handle can vary in size. In some embodiments, when the solid dosage form is placed inside a subject's oral cavity, the handle is large enough to protrude outside the subject's mouth. In some embodiments, when the solid dosage form is placed inside a subject's oral cavity, the handle is small enough to reside in the oral cavity when the mouth is closed.

The term "joint interface" refers to the area of contact between the handle and the solid oral dosage form. In some embodiments, the joint interface has an area of about 0.01 cm$^2$ to about 10 cm$^2$. In some embodiments, the joint interface has an area of about 0.1 cm$^2$ to about 1 cm$^2$.

Apparatuses that generate high frequency mechanical vibrations are known to those in the art. For example, in some embodiments the apparatus can comprise a Branson 2000 AED Actuator and a Branson 2000 D power supply (Branson, Danbury, Conn.). An apparatus for producing and transferring high frequency mechanical vibrations generally contains four parts: a power supply, a converter, an amplitude modifying device (commonly called a booster) and an acoustic tool known as the horn (or sonotrode). In some embodiments, high frequency mechanical vibrations are created by using a solid-state power supply to change 50/60 Hz electrical current into about 15, 20, 30, or 40 kHz electrical energy. This high frequency electrical energy is supplied to a converter, which transforms the electrical energy to mechanical motion at high frequencies. The mechanical motion, i.e., vibratory energy, is then transmitted through an amplitude-modifying booster to the horn. The horn transfers this vibratory energy directly to the parts being assembled.

The distance between the horn and the joint interface can vary. In some embodiments, the distance between the horn and the joint interface is about 0.1 μm to about 100 cm. In some embodiments, the distance between the horn and the joint interface is about 1 μm to about 50 cm, about 1 μm to about 25 cm, about 1 μm to about 20 cm, or about 1 μm to about 10 cm. In some embodiments, the distance between the horn and the joint interface is about 10 μm to about 1 cm. The horn can comprise various materials. In some examples, the horn material comprises aluminum or titanium.

In some embodiments, pressure can be applied to increase contact between the handle and the solid oral dosage form during application of the high frequency mechanical vibrations. In some embodiments, the pressure is about 1 psi to about 100 psi, or about 2 psi or about 50 psi. In some embodiments, the pressure is about 10 psi.

Various frequencies can be used in the present invention. The term "high frequency" refers to frequencies above 1 kHz. In some embodiments, high frequency refers to frequencies of about 1 kHz to about 10 MHz. In some embodiments, the high frequency mechanical vibrations have a frequency of about 5 kHz to about 100 kHz. In some embodiments, the high frequency mechanical vibrations have a frequency of about 15 kHz to about 40 kHz. In some embodiments, the high frequency mechanical vibrations are ultrasonic vibrations. The term "ultrasonic" refers to frequencies of sound energy higher than the upper limit of the human hearing range, about 20 kHz. In some embodiments, the ultrasonic frequencies are about 20 kHz to about 1 MHz. In some embodiments, the ultrasonic frequencies are about 20 kHz to about 500 kHz, about 20 kHz to about 200 kHz, or about 20 kHz to about 50 kHz.

Various types of vibrational energy can be used. In some embodiments the high frequency vibrations are linear vibrations. When using linear vibrations, frictional heat is generated by moving one part against the other under pressure through a linear displacement plane of the joint or amplitude. When a molten state is reached at the joint interface, vibration is stopped. Clamping pressure is maintained briefly while the molten material solidifies to form a bond. In some embodiments, the high frequency vibrations are orbital vibrations. Orbital vibrations use an electromagnetic drive to create a relative circular motion between the solid oral dosage form and the handle. This constant velocity motion generates heat, which raises the material temperature at the joint to its melting point. The motion is terminated after sufficient material is melted. The melted material then solidifies and forms a permanent bond.

Various oscillation amplitudes can be used in the present invention. In some embodiments, the high frequency mechanical vibrations have an oscillation amplitude of 1 μm to 1 cm. In some embodiments, the high frequency mechanical vibrations have an oscillation amplitude of 5 μm to 300 μm. In some embodiments, the high frequency mechanical vibrations have an oscillation amplitude of 10 μm to 100 μm.

The length of time used to apply the high frequency vibrations is dependent on several factors. These factors can include, but are not limited to, the composition of both the handle and the solid oral dosage form, the amount of pressure applied to the interface, the size of the joint interface between the handle and the solid oral dosage form, the frequency of the vibration, and the amplitude of the vibration. In some embodiments, the high frequency vibrations are applied for about 1 millisecond to about 30 seconds. In some embodiments, the high frequency vibrations are applied for about 0.1 second to about 10 seconds. In some embodiments, the high frequency vibrations are applied for about 0.1 second to about 5 seconds. In some embodiments, the high frequency vibrations are applied for about 1 second.

By applying high frequency mechanical vibrations to the joint interface, the solid oral dosage form at the joint interface can reach a molten state. The term "molten state" refers to the liquefied physical state of a material caused by heat.

In some embodiments, the solid oral dosage form further comprises an active agent. Various active agents can be used. In some embodiments, the active agent can be, but is not limited to, methohexital, pentobarbital, thiamylal, thiopental, fentanyl, modafinil, alfentanil, sufentanil, lofentanil, carfentanil, naloxone, epam, lorazepam, midazolam, oxazepam, triazolam, droperidol, propanidid, etomidate, propofol, ketamine, diprivan, bretylium, captopril, clonidine, dopamine, enalapril, esmolol, furosemide, isosorbide, labetalol, lidocaine, metolazone, metoprolol, nadolol, nifedipine, nitroglycerin, nitroprusside, propranolol, benzquinamide, meclizine, metoclopramide, prochlorperazine, trimethobenzamide, clotrimazole, nystatin, carbidopa, levodopa, sucralfate, albuterol, amninophylline, beclomethasone, dyphylline, epinephrine, flunisolide, isoetharine, isoproterenol HCl, metaproterenol, oxtriphylline, terbutaline, theophylline, ergotamine, methysergide, propranolol, suloctidil, ergonovine, oxytocin, desmopressin, acetate, lypressin, vasopressin, insulin, beta-endorphin, enkephalins, bradykinin, aniotensin I, gonadotropic hormones, adrenocorticotropic hormone (ACTH), calcitonin, parathyroid hormone, growth hormone, polysaccharides (such as heparin), salts or esters thereof, or combinations thereof. In some embodiments, the active agent is fentanyl or salt thereof, e.g., fentanyl citrate, or combinations thereof. In some embodiments, the active agent is fentanyl.

In the present invention, the handle can comprise various materials. In some embodiments, the handle comprises acetonitrile butadiene styrene, a thermoplastic, a semi-crystalline thermoplastic, an olefin, a thermostat polymer, a thermoplastic rubber, a composite plastic, or a mixture thereof. In some embodiments, the handle comprises a non-plastic material, e.g., a metal. In some embodiments, the handle comprises tubing.

The solid oral dosage form can be manufactured by different methods. In some embodiments, the active agent is added to a molten candy mass. The resultant mixture can then be thoroughly mixed to ensure proper distribution of the active agent within the molten candy mass. The mixture is then poured while still molten and allowed to solidify into a semi-solid mass. In some embodiments, the hot candy mass can be poured into molds, the size and shape of which can be determined as desired.

The solid oral dosage form can also be made by direct compression, injection molding, freeze-drying or other solid processing techniques. In some embodiments, the solid oral dosage form is a compressed dosage form. In some embodiments, the handle is in contact with the solid oral dosage form when the solid oral dosage form is being formed. For example, in a compressed dosage form, the handle can be present during the compression of solid oral dosage form. Thus, the handle is placed in a mold, the solid oral dosage form is formed around it. Alternatively, the solid oral dosage form can be formed in the absence of a handle, and then the handle can be placed in contact with the solid oral dosage form later. In some embodiments, the solid oral dosage form is formed with a cavity. In some embodiments, a portion of the handle can fit inside the cavity.

In some embodiments, method of making a solid oral dosage form attached to a handle further comprises employing a means for aligning the handle and the solid oral dosage form. The means for aligning are used to place the handle and the solid oral dosage form in the correct alignment with each other to ensure proper, repeatable alignment and to avoid marking during application of the high frequency mechanical energy. Various means for aligning the handle and the solid oral dosage form can be used. In some embodiments, the means for aligning can be, but is not limited to a pin, socket, tongue, groove, or combination thereof.

Having generally described the invention, a further understanding can be obtained by reference to the examples provided herein. These examples are for purposes of illustration only and are not intended to be limiting.

EXAMPLES

Example 1

A sugar-free solid oral dosage form comprising fentanyl was prepared using the formulation of Table 1.

TABLE 1

| SL# | INGREDIENTS | mg/dose |
|---|---|---|
| 1. | Fentanyl Citrate, USP | 0.6284 |
| 2. | Citric Acid, USP - Anhydrous (Powder) | 9.800 |
| 3. | Calcium Phosphate, Tribasic, NF | 828.0 |
| 4. | Povidone, USP (Plasdone K-29-32) | 100.0 |
| 5. | Polyethylene Glycol, NF (3350) | 150.0 |
| 6. | Crospovidone, NF (Polyplasdone XL) | 200.0 |
| 7. | Dibasic Calcium Phosphate Anhydrous, USP (A-Tab) | 549.6 |
| 8. | Hydrogenated Vegetable Oil, NF Type I (Lubritab) | 50.0 |
| 9. | Dibasic Sodium Phosphate, USP (Dried) | 31.00 |
| 10. | Aspartame Powder, NF (Nutrasweet ® Powder) | 36.00 |
| 11. | N—C Natural & Artificial Orange Flavor 884.114 (POWDER) | 30.00 |
| 12. | Magnesium Stearate, NF | 15.00 |
| 13. | Purified Water, USP | * |
| | Total weight per dose | 2000.00 |

* Purified water is excluded from the final formulation.

Tribasic calcium phosphate and an aqueous solution of fentanyl citrate were added to a Collette high shear mixer (Gral 120010) and mixed on low speed. Then tribasic calcium phosphate mixed with hydrogenated vegetable oil was added to mixer and the contents were remixed. Next, an aqueous solution of povidone was sprayed on the contents in the mixer and the contents were then remixed.

The mixture was then discharged from the mixer, passed through a co-mill, and dried in a fluid bed dryer. The resulting dried powder was passed through a screen and again placed in a Collette high shear mixer. Aspartame, citric acid, polyethylene glycol, dibasic calcium phosphate anhydrous, and flavoring were then added to the mixer and the contents were mixed. Finally, magnesium stearate and crospovidone were added to the mixer and the contents were remixed. The resulting powder was then compressed to form an oral transmucosal dosage form.

Example 2

A handle, made of acetonitrile butadiene styrene, was ultrasonically welded to the solid oral dosage form of Example 1. The ultrasonic welding was performed by applying high frequency vibrations to the handle for one second using a Branson 2000 AED Actuator and Branson 2000 D power supply. The settings on the Branson 2000 AED Actuator and a Branson 2000 D power supply are found in Table 2. These settings are based upon a 30 kHz machine with a 1500 watt converter (CA30) and using a booster of 1:2.5.

TABLE 2

| Instrument Variable | Setting |
|---|---|
| Air PSI | 10 lbs |
| Energy | 30 joules |
| Amplitude | 30%–40% |
| Pretrigger Amplitude | 25%–40% |
| Down Speed | 15 |
| Hold Time | 1 second |
| Trigger Force | 10 lbs |
| Time Out | 6 seconds |

The vibrations, through surface and intramolecular friction, produced a sharp rise in temperature at the joint interface between the handle and the lollipop matrix, causing the matrix around the joint interface to melt. When the vibrations stopped, the lollipop matrix material solidified, resulting in a weld between the handle and the lollipop matrix. Once the lollipop matrix had solidified, the attachment bond strength was 44.9 pounds, as determined using a Chatillon TCD 201 MF series pull force tester and a Chatillon DFA-50 digital force gauge.

Example 3

A solid oral dosage form comprising fentanyl was prepared using the formulation of Table 3.

TABLE 3

| SL# | INGREDIENTS | mg/dose |
|---|---|---|
| 1. | Fentanyl Citrate, USP | 0.6284 |
| 2. | Confectioner's Sugar, USP | 1255 |
| 3. | Dextrates, NF Hydrated (EMDEX ®) | 598.59 |
| 4. | Citric Acid, USP - Anhydrous (granular) | 9.8 |
| 5. | Dibasic Sodium Phosphate, USP (dried) | 31.00 |
| 6. | Pregelatinized Starch, NF (National 1551) | 80.0 |
| 7. | Raspberry Flavor | 10.0 |

TABLE 3-continued

| SL# | INGREDIENTS | mg/dose |
|---|---|---|
| 8. | Magnesium Stearate, NF | 15.00 |
| 9. | Purified Water, USP | * |
| | Total weight per dose | 2000.0 |

* Purified water is excluded from the final formulation.

The sugar and pregelatinized starch were mixed in a Collette high shear mixer (Gral 10) on low speed. Fentanyl and citric acid were dissolved in water, and then sprayed onto the sugar/starch mixture while mixing. The resulting mixture was then wet milled, subjected to fluid bed drying, and then dry milled in a Fitzmil. The dry milled mixture was mixed with the remaining ingredients using a V-blender. The resulting powder was then compressed to form a solid oral dosage form. The solid oral dosage form (without the handle attached) can be used as a lozenge.

Example 4

A handle, made of acetonitrile butadiene styrene, was ultrasonically welded to the solid oral dosage form of Example 3 using a Branson 2000 AED Actuator and a Branson 2000 D power supply. The settings on the Branson 2000 AED Actuator and Branson 2000 D power supply are found in Table 4. These settings are based upon a 30 kHz machine with a 1500 watt converter (CA30) and using a booster of 1:2.5.

TABLE 4

| Instrument Variable | Setting |
|---|---|
| Air PSI | 10 lbs |
| Energy | 30 joules |
| Amplitude | 20%–35% |
| Pretrigger Amplitude | 20%–35% |
| Down Speed | 15 |
| Hold Time | 1 second |
| Trigger Force | 10 lbs |
| Time Out | 6 seconds |

The vibrations caused the matrix around the joint interface to melt. When the vibrations stopped, the lollipop matrix material solidified, resulting in a weld between the handle and the lollipop matrix. Once the lollipop matrix had solidified, the attachment bond strength was 57.4 pounds, as determined using a Chatillon TCD 201 MF series pull force tester and a Chatillon DFA-50 digital force gauge.

These examples illustrate possible methods of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed:

1. A method of attaching a handle to a solid oral dosage form, the method comprising:
    placing a handle in contact with a solid oral dosage form, wherein an area of contact between the handle and the solid oral dosage form forms a joint interface;
    applying high frequency mechanical vibrations to the joint interface until a localized melting of the solid oral dosage form at the joint interface is achieved; and
    cooling the joint interface in a molten state to allow solidification, thereby attaching the handle to the solid oral dosage form.

2. The method of claim 1, wherein the joint interface has an area of about 0.01 cm$^2$ to about 10 cm$^2$.

3. The method of claim 1, wherein the high frequency mechanical vibrations are generated by a horn, and wherein the distance between the horn and the joint interface is about 1 μm to about 25 cm.

4. The method of claim 1, wherein pressure is applied to increase contact between the handle and the solid oral dosage form during application of the high frequency mechanical vibrations.

5. The method of claim 4, wherein the pressure is about 1 psi to about 100 psi.

6. The method of claim 1, wherein the high frequency mechanical vibrations are ultrasonic vibrations.

7. The method of claim 6, wherein the ultrasonic vibrations are linear vibrations.

8. The method of claim 6, wherein the ultrasonic vibrations are orbital vibrations.

9. The method of claim 1, wherein the high frequency mechanical vibrations have a frequency of about 5 kHz to about 100 kHz.

10. The method of claim 1, wherein the high frequency mechanical vibrations have a frequency of about 15 kHz to about 40 kHz.

11. The method of claim 10, wherein the high frequency mechanical vibrations have an oscillation amplitude of about 5 μm to about 300 μm.

12. The method of claim 1, wherein the high frequency mechanical vibrations have an oscillation amplitude of about 10 μm to about 100 μm.

13. The method of claim 1, wherein the solid oral dosage form comprises an active agent.

14. The method of claim 13, wherein the active agent is fentanyl, fentanyl citrate, or combinations thereof 15. The method of claim 1, wherein the handle comprises acetonitrile butadiene styrene, a thermoplastic, a semi-crystalline thermoplastic, a thermostat polymer, an olefin, a thermoplastic rubber, a metal, a composite plastic, or a mixture thereof 16. The method of claim 1, wherein the solid oral dosage form is a compressed dosage form.

17. The method of claim 1, wherein the solid oral dosage form is a molded dosage form.

18. The method of claim 1, wherein the handle is a rigid rod.

19. The method of claim 1, wherein the high frequency vibrations are applied for about 0.1 seconds to about 10 seconds.

20. The method of claim 1, further comprising employing a means for aligning the handle and the solid oral dosage form.

21. The method of claim 20, wherein the means for aligning is selected from the group consisting of a pin, socket, tongue, groove, or combination thereof.

22. A method of attaching a handle to a solid oral dosage form, the method comprising:
applying high frequency mechanical vibrations until localized melting is achieved between a handle and a solid oral dosage form that are in contact with one another; and
cooling the handle and the solid oral dosage form to provide a bond there between.

* * * * *